(12) United States Patent
Waldrop, III (10) Patent No.: US 11,478,288 B1
(45) Date of Patent: Oct. 25, 2022

(54) APPARATUS AND METHOD FOR A STABILIZATION NAIL

(71) Applicant: Robert Alison Waldrop, III, Scottsdale, AZ (US)

(72) Inventor: Robert Alison Waldrop, III, Scottsdale, AZ (US)

( * ) Notice: Subject to any disclaimer, the term of this patent is extended or adjusted under 35 U.S.C. 154(b) by 0 days.

(21) Appl. No.: 17/352,088

(22) Filed: Jun. 18, 2021

Related U.S. Application Data (63) Continuation of application No. 17/349,127, filed on Jun. 16, 2021, now abandoned.

(51) Int. Cl.
*A61B 17/84* (2006.01)
*A61B 17/86* (2006.01)
*A61B 17/70* (2006.01)
*A61B 17/56* (2006.01)

(52) U.S. Cl.
CPC ........ *A61B 17/846* (2013.01); *A61B 17/7002* (2013.01); *A61B 17/7032* (2013.01); *A61B 17/8625* (2013.01); *A61B 2017/564* (2013.01)

(58) Field of Classification Search
CPC .............. A61B 17/846; A61B 17/7002; A61B 17/7032; A61B 17/8625; A61B 17/1728; A61B 17/1725; A61B 17/8061; A61B 17/72; A61B 17/7037; A61B 17/7056; A61B 17/7052; A61B 17/7055; A61B 17/7038; A61B 17/7041; A61B 2017/564

USPC .................................. 606/246–279, 300–321
See application file for complete search history.

(56) References Cited

U.S. PATENT DOCUMENTS

| | | | | |
|---|---|---|---|---|
| 9,044,272 B2 * | 6/2015 | Shaffrey | ............ | A61B 17/7002 606/266 |
| 9,522,066 B2 * | 12/2016 | Segina | ................ | A61B 17/1728 |
| 2009/0069812 A1 * | 3/2009 | Gillard | ................ | A61B 17/7233 606/62 |
| 2013/0053854 A1 * | 2/2013 | Schoenefeld | .......... | A61B 90/92 606/87 |
| 2018/0360500 A1 * | 12/2018 | Butler | ................ | A61B 17/7002 |
| 2019/0290329 A1 * | 9/2019 | Bess | ................ | A61B 17/7053 |

* cited by examiner

*Primary Examiner* — Tessa M Matthews
(74) *Attorney, Agent, or Firm* — Inspired Idea Solutions Law Firm (57) ABSTRACT

A method and apparatus is disclosed for the surgical installation of a nail for stabilizing a screw-rod configuration attached to vertebrae of a spine to the rib cage of an organic body to treat Adult Spinal Deformity (ASD) and prevent proximal junctional failure (PJF). The nail may be secured at one end to an adjacent rib of the rib cage, and may extend into the rib or be secured to the rib by a rib hook. The nail may be secured at another end to a rod of the screw-rod configuration, such that the nail imparts stability from the rib cage to the screw-rod configuration and to the vertebrae of the spine.

8 Claims, 5 Drawing Sheets

APPARATUS AND METHOD FOR A STABILIZATION NAIL

FIELD

The present disclosure generally relates to treatment of adult spinal deformity (ASD), and more particularly to use of a nail to prevent proximal junctional failure (PJF).

BACKGROUND

Adult spinal deformity (hereinafter "ASD") has been identified as a global health problem that affects most age groups, but particularly the elderly aged above 65 years old. While the classification system of ASD has yet to be standardized worldwide, it is recognized as a condition which has a profound impact on life expectancy, the ability to engage in physical activity, and overall quality of life.

ASD may take many forms, and has been classified based on severity, etiology, radiographic distinctions, neutral upright spinal alignment, or based on any number of pelvic sagittal or other parameters for measurement of the spine (e.g., pelvic incidence, sacral slope, pelvic tilt, lumbar lordosis, thoracic kyphosis, sagittal vertical axis, vertebral body height, proximal junctional angle, lordotic angle, kyphotic angle, and so forth).

Because ASD almost universally gets worse with time, patients suffering from ASD often undergo spinal deformity surgery in an attempt to correct spinal deformities. Surgeries of this type generally include the installation of a number of pedicle screws (e.g., screws connected to the vertebra at the pedicle), or other screw placements along the spine (e.g., cortical or bicortical fixation), with a rod extending along the spine and interconnected with the screws to stabilize each vertebra. While this treatment has been shown to correct the underlying deformity, such as correcting the spinal parameters measured to diagnose ASD, it can also cause post-surgery complications in a large number of patients, sometimes in as many as 70% of patients, depending on the type and severity of the ASD.

Surgery may slow the degeneration for some, but surgeries can and often do result in post-surgery complications, such as proximal junctional kyphosis, a deformation in the proximal part of the spinal construct, or proximal junctional failure (hereinafter "PJF"), a more serious condition where the spinal structure has failed causing increased pain and neurological disorders. PJF may occur between the upper instrumented vertebra (hereinafter "UIV") and the next vertebra (hereinafter "UIV+1"), the most common area of failure, or between UIV+1 and the next vertebra (hereinafter "UIV+2"), and so on.

PJF may occur due to vertebral body fracture, or bony failure; due to ligament complex failure; or due to instrument failure, such as the failure of implants or pullout of screws from the spinal vertebra. Therefore, it has been the focus of experts in the field to better classify ASD and discover better ways to prevent degeneration in patients, in particular to reduce the instance of PJF.

SUMMARY

A screw-rod configuration comprises one or more screws interconnectable with a plurality of vertebrae of an organic body, the screws having a head portion and a threaded portion; one or more rods interconnectable with the one or more screws at the head portion; and one or more nails interconnectable with the one or more rods, the one or more nails extending substantially orthogonally from the one or more rods.

A screw-rod configuration comprises one or more screws interconnectable with a plurality of vertebrae of an organic body, the screws having a head portion and a threaded portion; one or more rods interconnectable with the one or more screws at the head portion; and one or more nails interconnectable with the one or more rods, the one or more nails extending from a head portion coupled to the one or more rods toward an elongated portion, the elongated portion secured to one or more ribs.

A method of surgically installing a nail to stabilize a screw-rod configuration comprises securing an elongated portion of a nail to a rib adjacent to the screw-rod configuration; and securing a head portion of the nail to a rod of the screw-rod configuration.

BRIEF DESCRIPTION OF THE DRAWINGS

Various aspects and advantages will become apparent upon review of the following detailed description and upon reference to the drawings in which.

DETAILED DESCRIPTION

The following disclosure includes a method and apparatus for stabilizing the spine with a screw-rod configuration and a stabilization nail extending from the screw-rod configuration to adjacent ribs.

Figure 1:
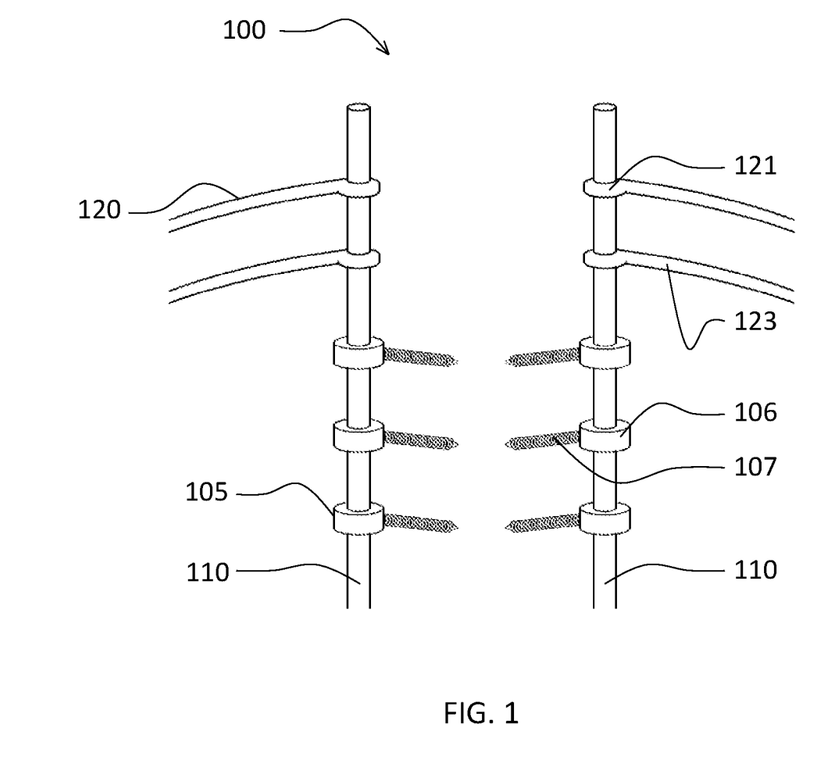
FIG. 1 illustrates an isometric view of screw-rod configuration for treating ASD including one or more stabilization nails.

FIG. 1 illustrates an isometric view of screw-rod configuration 100 for treating ASD. The screw-rod configuration 100 may include one or more screws 105, one or more rods 110, and one or more nails 120. The one or more screws 105 may be secured to any number of vertebrae in any number of screw trajectories (e.g., screw trajectory 208 of FIG. 2B). Screws 105 may have a head portion 106 secured to a threaded portion 107. While the vertebrae are not illustrated in FIG. 1, the threaded portion 107 of each of the one or more screws 105 may be dimensioned to be secured at least partially or entirely within a corresponding vertebra along a screw trajectory. Further, the head portion 106 of each of the one or more screws 105 may be optimally positioned to extend outwardly from the corresponding vertebra (e.g., mono-axially, or poly-axially, along the screw trajectory).

The one or more rods 110 may extend along a rod trajectory defined by its path (e.g., a linear path, an arcuate path of constant curvature, an arcuate path of irregular curvature, and so forth). Further, the one or more rods 110 may extend across the one or more screws 105 (e.g., extending across each head portion 106). Further, the one or more rods 110 may be secured to each of the one or more screws 105 at the head portion 106. Therefore, it may be advantageous to position the one or more screws 105 such that the corresponding screw trajectory of each of the one or more screws 105 intersects with the rod trajectory, and/or it may be advantageous to configure the one or more rods 110 with a rod trajectory that intersects the screw trajectory of each of the one or more screws 105 in its path. Each of the one or more screws 105 may be interconnected with a corresponding rod 110 to prevent their movement with respect to each other. Rod 110 may be inserted into head portion 106 and may be secured by a locking nut, end cap, by clamping, or by other means known in the art.

As illustrated in FIG. 1, the screw-rod configuration 100 may incorporate a first rod 110 and a second rod 110 extending along a spine of the patient (e.g., positioned to extend along opposing sides of the vertebrae). The use of first and second rods 110 positioned oppositely may provide symmetrical support to the spine of the patient, though it is contemplated by the present invention that a fewer or greater number of rods may be positioned along the spine. The spine of the patient requiring surgical connection of the screw-rod configuration 100 may be the cervical portion, the thoracic portion, the lumbar portion, or the sacrum/coccyx portion of the spine.

The one or more screws 105 may incorporate any number of screws 105 (e.g., two, three, four, five, six, seven, eight, nine, ten, eleven, twelve, or more screws) to optimally stabilize the spine, collectively, or each vertebra, individually. Further still, each vertebra (e.g., vertebra 280 of FIG. 2A) may be configured with any number of screws (e.g., one, two, three, four, or more screws) to optimally orient and/or stabilize the vertebra with respect to the screw-rod configuration 100 (e.g., two screws positioned oppositely on the vertebra to accommodate two opposing rods extending along the spine). Thus, connection of one or more rods 110 to one or more screws 105 may stabilize the UIV with the UIV+1, UIV+2, or any number of additional vertebrae (UIV+3, UIV+4, UIV+5, UIV+6, UIV+7, UIV+8, UIV+9, UIV+10, or additional vertebrae).

Figure 3:
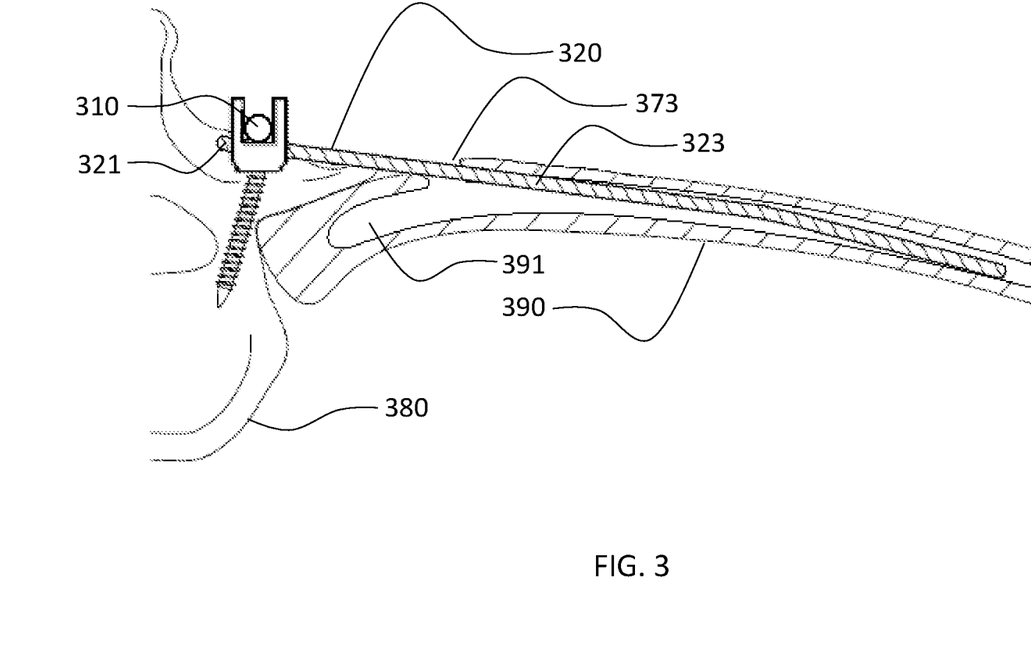
FIG. 3 illustrates a cross sectional view of a rib with a stabilization nail inserted into the rib.

One or more nails 120 may extend from the one or more rods 110 to one or more ribs (e.g., ribs 390 of FIG. 3). The one or more nails 120 may have a head portion 121 and an elongated portion 123. The head portion 121 may be configured to be securable to the one or more rods 110 (e.g., in the same, a similar manner, or a different manner of interconnection of the one or more screws 105 and the one or more rods 110 (e.g., via set screws, clamps, screws, or other fasteners). The elongated portion 123 may extend approximately orthogonally (e.g., ninety degrees plus or minus thirty degrees) away from the one or more rods 110 toward one or more ribs (e.g., ribs 490 of FIG. 4). Further, the elongated portion 123 may extend at an incline to the path of the rib, or rib trajectory, so as to come into close proximity with and/or contact with the rib.

The one or more nails 120 may be positioned along the one or more rods 110 between the one or more screws 105, above the one or more screws 105 (e.g., as exemplified in FIG. 1), below the one or more screws 105, or in any combination thereof. Thus, a first nail 120 may extend from a first rod above an uppermost screw of the one or more screws 105 and a second nail 120 may extend from a first rod above the uppermost screw of the one or more screws 105 (as exemplified in FIG. 1). Further, a first nail 120 may extend from a first rod above an uppermost screw of the one or more screws 105 and a second nail 120 may extend from a first rod between the uppermost screw and a second screw of the one or more screws 105.

A person of ordinary skill in the art will appreciate that various configurations are possible. The terms "above" and "below" are understood to be relative terms, but in general below indicates a position below the UIV and/or below the screw-rod configuration 100, and above indicates a position above the last UIV+ interval and/or above the screw-rod configuration 100 (e.g., below and above are understood to be on opposing ends of the screw-rod configuration 100).

The one or more nails 120 may be dimensioned to optimize performance after installation in the patient. The length of the one or more nails 120 may vary to enable interconnection with one or more ribs (e.g., ribs 390 of FIG. 3) at different points along the one or more ribs. Thus, the nail lengths may be between about 10 and about 150 millimeters (hereinafter "mm"). Further, the nail lengths may be of standardized lengths of an incremental nature (e.g., intervals of 1, 2, 5, 10, or other intervals). Thus, the nail lengths may be standardized at 5 mm intervals (e.g., 40, 45, 50, 55, 60, 65, and so on). A person of ordinary skill in the art will appreciate that any variation of lengths is possible to facilitate attachment of the screw-rod configuration 100 to the one or more ribs (e.g., ribs 390 of FIG. 3) via the one or more nails 120.

The gauge of the one or more nails 120 may vary to enable interconnection with differently sized ribs (e.g., ribs 390 of FIG. 3). The gauge of the one or more nails 120 may vary to enable various amounts of elasticity (e.g., depending on which rib it is secured to, which region of the patient's back it is secured within, or based on other criteria). Thus, the gauge of the one or more nails 120 may be uniform along its length, or variable to enable greater flexibility at discrete positions along its length. Where two or more nails 120 are used in a single surgery, each nail may have a different gauge selected based on the above criteria. A person of ordinary skill in the art will appreciate that any variation of gauges is possible to facilitate flexibility and/or elasticity of the interconnection between the screw-rod configuration 100 and the one or more ribs (e.g., ribs 490 of FIG. 4).

The material (e.g., titanium, stainless steel, or other material) of the one or more nails 120 may be selected to enable various amounts of elasticity, durability, or longevity within the organic body (e.g., the human body). A person of ordinary skill in the art will appreciate that material selection may be optimized to facilitate flexibility and/or elasticity of the interconnection between the screw-rod configuration 100 and the one or more ribs (e.g., ribs 390 of FIG. 3). The one or more nails 120 may be constructed linearly (e.g., prior to exerting any force on the one or more nails 120), with an arcuate path of constant curvature, or with an arcuate path of irregular curvature. The shape of the one or more nails 120 may define a nail trajectory, and nail trajectories may be selected based on the desired path of each nail as it passes from the screw-rod configuration 100 to a corresponding rib.

Thus, any of the above design considerations may be optimized such that the one or more nails 120 may increase the stabilization of the screw-rod configuration 100 in the organic body. Thus, the one or more nails 120 may rely on the organic stability of the rib cage (e.g., one or more ribs of the rib cage) to stabilize the screw-rod configuration 100. The increased stabilization of the screw-rod configuration 100 by the one or more nails 120 may reduce the stress exerted between the UIV and UIV+1 vertebrae, between the UIV+1 and UIV+2 vertebrae, and so forth (e.g., between all adjacent vertebrae coupled to screw-rod configuration 100). Further, the increased stabilization may provide a number of benefits to the patient, such as reducing vertebral body fracture, reducing bony failure, reducing ligament complex failure, reducing instrument failure, reducing implant dislocation, reducing screw pullout, and so forth.

Stabilization of the screw-rod configuration 100 to adjacent ribs as a treatment option (or any spinal fixation system) during surgery also enjoys a significant amount of versatility in that it can be used in connection with any and all other known treatment options, screw configurations, implants, cementous augmentations and other instruments.

The one or more rods 110 may be dimensioned to optimize performance after installation in the patient. Thus, the length of the one or more rods 110 may be dimensioned to extend across, through, or adjacent to all of the one or more screws 105 and/or the one or more nails 120 in its path (e.g., where the one or more nails 120 are positioned above, below, in between the one or more screws 105, or any combination thereof). A person of ordinary skill in the art will appreciate that a surgeon will select a rod of appropriate length to accommodate all screws and nails in the system and to achieve a successful surgery outcome.

Further, the gauge of the one or more rods 110 may be dimensioned to enable a desired amount of flexibility (e.g., to enable the patient to bend and move during normal life activities). The gauge of the one or more rods 110 may be uniform and/or variable along the length of the one or more rods to enable flexibility and performance (e.g., based on where along the spine the one or more rods 110 are located, or based on other criteria). A person of ordinary skill in the art will appreciate that a surgeon will select a rod of appropriate gauge to optimize performance and to achieve a successful surgery outcome.

While the present disclosure has discussed the use of one or more screws 105, the present disclosure uses the words "screw" or "screws" to mean any fastener configured to fasten to any part or portion of the vertebrae (e.g., pedicle, cortical, or otherwise). Thus, "screws" may be screws in the traditional sense (e.g., having a length and a helical threading along its length, screws having circular threading, a shaft extending into the vertebra with a frictional fit, a shaft extending into the vertebra having protrusions configured to be retained by a cementous mixture inserted into the vertebra, a loop extending into the vertebra configured to be retained by a cementous mixture inserted into the vertebra, or any other known means for securing a rod along the length of a spine.

Figures 2A, 2B:
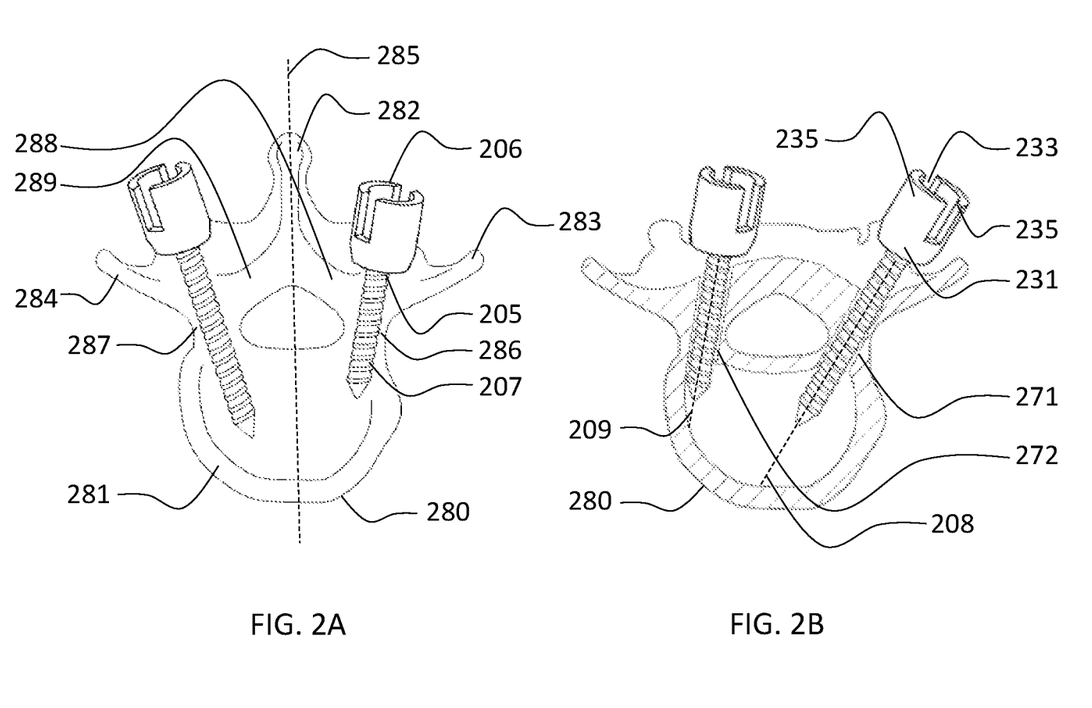
FIG. 2A illustrates a cross sectional view of a spinal vertebra having screws attached to the vertebra.
FIG. 2B illustrates a cross sectional view of a spinal vertebra having screws attached to the vertebra.

FIGS. 2A and 2B illustrate cross sectional views of spinal vertebrae 280 having one or more screws 205 of a screw-rod configuration (e.g., screw-rod configuration 100 of FIG. 1) attached to the vertebrae (e.g., cervical vertebrae, thoracic vertebrae, lumbar vertebrae, sacrum vertebrae, etc.). The one or more screws 205 may have a head portion 206 secured to a threaded portion 207. The threaded portion 207 of each of the one or more screws 205 may be dimensioned to be secured at least partially or entirely within vertebra 280 along a screw trajectory 208. Further, the head portion 206 of each of the one or more screws 205 may be optimally positioned to extend outwardly from vertebra 280 (e.g., poly-axially, at an incline with respect to the screw trajectory and/or mono-axially, in line with respect to the screw trajectory).

Head portion 206 may include a neck portion 231 with a slot 233 extending through the neck portion 231 to form at least two opposing sidewalls 235. During interconnection of a rod (e.g., rod 110 of FIG. 1) to the one or more screws 205, the rod may be inserted between the two opposing sidewalls 235 and/or into slot 233. An end cap (not shown) may be secured to the two opposing sidewalls 235 to retain and/or secure the rod within slot 233.

In general, vertebra may vary in size, shape and the prominence of various features along the length of the spine (e.g., such as the difference between the vertebra 280 of FIG. 2A and the vertebra 280 of FIG. 2B). Nevertheless, vertebra 280 may have a vertebral body 281 on the anterior side of the vertebra, and further may have a spinous process 282 on the posterior side of the vertebra. A right transverse process 283 and left transverse processes 284 may extend outwardly from a plane of symmetry 285 extending through the vertebral body 281 and spinous process 282. Right transverse processes 283 may be interconnected with the vertebral body 281 by a right pedicle 286, and left transverse processes 284 may be interconnected with the vertebral body 281 by a left pedicle 287. Further, right transverse processes 283 may be interconnected with the spinous process 282 by a right lamina 288, and left transverse processes 284 may be interconnected with the spinous process 282 by a left lamina 289 (e.g., forming the spinal canal, extending through the middle of the vertebral body 281, the spinous process 282, and the right and left transverse processes 283, 284).

A pedicle aperture 271 and/or a cortical aperture 272 may be formed in the space between the spinous process 282 and either the right or left transverse processes 283, 284 to enable insertion of the one or more screws 205. Whereas a pedicle aperture 271 is located closer to the right or left transverse processes 283, 284, a cortical aperture 272 originates closer to the spinous process 282. The one or more screws 205 may extend from the posterior side of vertebra 280 through the cortex (e.g., either of the apertures 271, 272) into the interior of the vertebra 280. The one or more screws 205 may pass through the right or left pedicles 286, 287 into the vertebral body 281 (i.e., this path defining the screw trajectory).

A screw passing through pedicle aperture 271 (e.g., closer to the right or left transverse processes 283, 284) passes through the right or left pedicles 286, 287 and substantially into an interior of the vertebral body 281 away from the cortex of the vertebral body 281 (e.g., defining a pedicle screw trajectory). A screw passing through cortical aperture 272 (e.g., closer to the spinous process 282) passes through the right or left pedicles 286, 287 and substantially along a side of the vertebral body 281 (e.g., defining a cortical screw trajectory). In either case, care must be taken to ensure that the cortex of the vertebral body 281 is not punctured by the threaded portion 207 as it is inserted into vertebra 280.

Threaded portion 207 may be dimensioned to optimize attachment of a rod (e.g., rod 110 of FIG. 1) to vertebra 280. Thus, threaded portion 207 may be selected for length, threading, gauge, or other criteria to facilitate attachment of head portion 206 to vertebra 280. A longer threaded portion 207 may be utilized for screw trajectory 208 (e.g., a pedicle screw trajectory), whereas a shorter threaded portion 207 may be utilized for screw trajectory 209 (e.g., a cortical screw trajectory). Thus, a person of ordinary skill in the art may select a screw length based on the desired screw trajectory, the size of the vertebra 280 or based on other criteria.

Further, threaded portion 207 may be selected based on threading size, or threading spacing. A threaded portion 207 having a first threading size and a first threading spacing may be selected for use in connection with pedicle aperture 271, whereas a threaded portion 207 having a second threading size and a second threading spacing may be selected for use in connection with cortical aperture 272.

Further, a threaded portion 207 may have a first threading size and a first threading spacing along a first portion of its length and a second threading size and a second threading spacing along a second portion of its length (e.g., the first size/spacing configured to engage one of the apertures 271, 272, and the second size/spacing configured to engage the right or left pedicles 286, 287). A person of ordinary skill in the art will appreciate that various combinations of similar or different sizes/spacings of threading may be employed to maximize retention of head portion 206 to vertebra 280.

Further, threaded portion 207 may be selected based on the gauge of the threaded portion 207 (e.g., the thickness of the shaft), to accommodate differently sized apertures 271, 272 and/or differently sized vertebra 280 (e.g., differently sized pedicles).

FIG. 3 illustrates a cross sectional view of a rib 390 with a nail 320 inserted into the rib 390. The nail 320 may have a head portion 321 and an elongated portion 323 extending from the head portion. Head portion 321 may be secured to a rod 310, such that the elongated portion 323 may extend from rod 310 toward rib 390. Further, the elongated portion 323 may extend to a surface of rib 390 (e.g., as exemplified in FIG. 4), or may extend into rib 390 (e.g., through a dorsal aperture 373 in the cortex of the rib), or both.

In general, rib 390 may extend from vertebra 380 at the vertebral body (e.g., vertebral body 281 of FIG. 2A) and adjacent to the right or left transverse processes (e.g., right and left transverse processes 283, 284 of FIG. 2A). As the vertebral body is on the anterior side of the vertebra, and the transverse processes are located closer to the posterior of the vertebra, ribs generally extend from the vertebral body at a relatively steep angle toward the exterior of the organic body (e.g., a human body), then curve to a relatively shallow angle, or roughly parallel, to the exterior of the organic body (e.g., the dorsal portion, or tubercle of the rib, near the dorsal aperture 373).

Thus, elongated portion 323 may extend through a dorsal aperture 373, may pass into the interior 391 of rib 390, and may pass a discrete distance through the interior 391 of rib 390. The length of elongated portion 323 may be selected to pass a discrete distance through the interior 391 of rib 390 without causing damage to rib 390. Further, rib 390 may impart stability to the elongated portion 323 by virtue of its proximity to and connection with other ribs in the rib cage. Thus, the stability imparted to elongated portion 323 may be passed on to its corresponding head portion 321 and on to a corresponding screw-rod configuration (e.g., screw-rod configuration 100 of FIG. 1).

While dorsal aperture 373 has been described as being formed near the dorsal of rib 390, various other aperture locations are contemplated by this disclosure that will serve to provide stability to the elongated portion 323 of nail 320. A person of ordinary skill in the art will appreciate that a surgeon may select an aperture location for convenience of inserting the elongated portion 323, alignment with the rod or screw-rod configuration, or based on other criteria.

Figure 4:
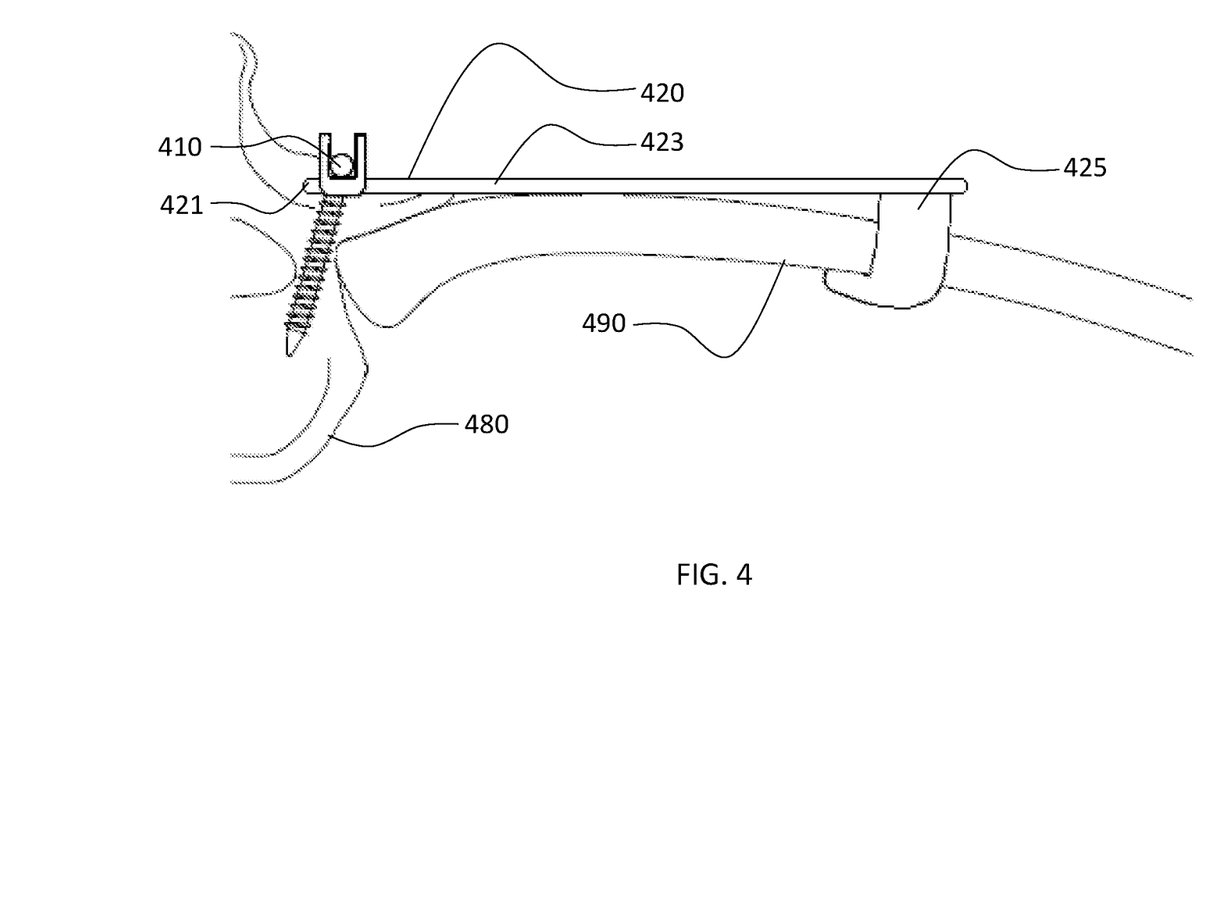
FIG. 4 illustrates an isometric view of a rib with a stabilization nail secured to the rib.

FIG. 4 illustrates an isometric view of a rib 490 with a nail 420 secured to the rib 490 and corresponding to a vertebra 480. The nail 420 may have a head portion 421 and an elongated portion 423 extending from the head portion. Head portion 421 may be secured to a rod 410, such that the elongated portion 423 extends from the rod toward rib 490. Further, the elongated portion 423 may extend into rib 490 (e.g., as exemplified in FIG. 3), or may extend to a surface of rib 490 (e.g., to a rib hook 425 secured around the rib 490), or both.

Rib hook 425 may pass partially around rib 490 (e.g., clamped), entirely around rib 490 (e.g., strapped), or may be of a similar type or function to the screws described in this disclosure (e.g., bored into rib 490). In any case, rib hook 425 may be configured to receive and be secured to nail 420. The type and manner of interconnection of rib hook 425 to nail 420 may vary depending on accessibility of rib 490, shape of rib 490, size of rib 490, shape of rib hook 425, or based on other criteria, and may be selected to optimize stabilization of nail 420 on rib 490.

Figure 5:
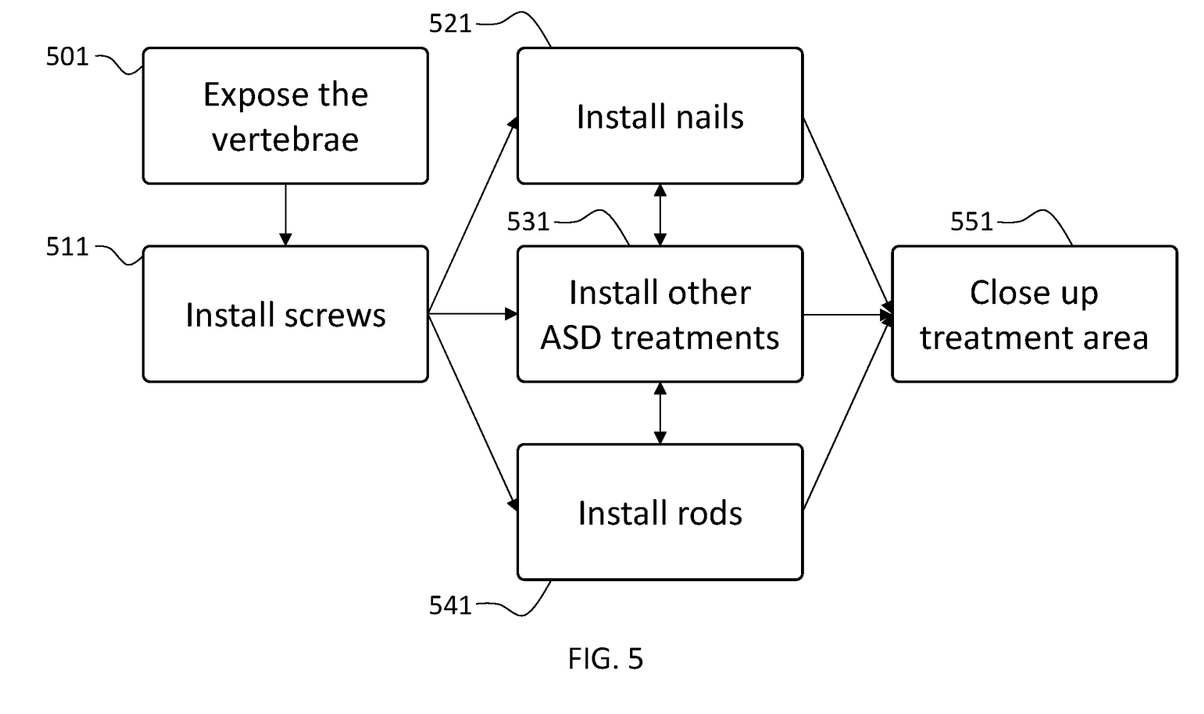
FIG. 5 illustrates a block diagram of a method of installing a stabilization nail.

FIG. 5 illustrates a block diagram of a method of installing a screw-rod configuration and one or more stabilization nails. In the method of installing the screw-rod configuration and the corresponding one or more nails, a surgeon may perform many of the same surgical steps proscribed in known ASD treatments, such as at step 501, exposing the vertebrae. Exposing the vertebrae may include creating one or more incisions in the organic tissue and peeling back the skin of the patient to expose the portion of the spine (and ribs) where treatment is to occur (e.g., the vertebrae where PJF has occurred).

In another step, such as step 511, a surgeon may install the screws to each vertebra, respectively, to undergo the treatment. The type of screw used (e.g., pedicle vs. cortical), it's various characteristics (as presented in this disclosure), and the screw trajectory may be selected by the surgeon by using the intersection technique or other optimization techniques (e.g., using a pedicle probe, pedicle sounding device, or other image/audio guidance to navigate the isthmus into the vertebral body. Further, the aperture formed in each vertebra may be formed using a pedicle awl or burr to open the superficial cortex of each vertebra. Great care should be taken to ensure no breach is formed in the anterior cortex. Selected screws may be threaded into the aperture and/or may be further reinforced using a Cementous mixture inserted into the vertebral body prior to threading of the screws. It is understood that the screws are mounted in such a way as to create an approximate path (e.g., the rod trajectory) extending along each vertebrae in the spine.

In another step, such as step 521, a surgeon may install the nails on and/or into each rib, respectively, that has been selected to provide stabilization to the screw-rod configuration. The surgeon may select nails based on its various characteristics (as presented in this disclosure) and the nail trajectory to optimize stabilization of the screw-rod configuration. Where a nail is to pass into the interior of a rib, the surgeon may employ the use of similar instruments and tools identified above with respect to screw insertion to create an aperture in the rib and measure the extent to which the nail may be inserted into the rib without causing damage. The nail may be inserted and oriented so that it extends above, between, or below the screws mounted to the vertebrae. Where a nail is to pass along the exterior of a rib, the surgeon may be required to expose enough of the rib to enable securement of a rib hook to the rib and attachment of the nail to the rib hook so that the nail extends above, between, or below the screws mounted to the vertebrae. It is understood that the nails are mounted in such a way as to intersect the approximate path (e.g., the rod trajectory) extending along each vertebrae in the spine.

In another step, such as step 531, a surgeon may install any other ASD treatments which the surgeon determines would be a benefit to the patient. This step may occur before or after step 521, as determined in the discretion of the surgeon and depending on the type of treatment. This step may occur before or after step 541, as determined in the discretion of the surgeon and depending on the type of treatment.

In another step, such as step 541, a surgeon may install the rods by placing each rod along the approximate path (e.g., the rod trajectory) formed by the screws and the nails. Once in place, the rod may be secured to each screw and nail in its path (e.g., sequentially from bottom to top, sequentially from top to bottom, or non-sequentially).

In another step, such as step 551, a surgeon may complete the surgery by enclosing the treatment area. The treatment area may be enclosed by pulling skin back over the spine and/or sealing the opening using known techniques (e.g., stiches, cauterization, etc.). In addition, it may be necessary to provide other type of treatments when closing up the treatment area, such as applying antibiotics, forming stiches in the ligament complex, or other types of wound care.

Other aspects will be apparent to those skilled in the art from consideration of the specification and practice disclosed herein. It is intended, therefore, that the specification and illustrated embodiments be considered as examples only.

What is claimed is:

1. A method of surgically installing a first nail to stabilize a screw-rod configuration, the method comprising:
   securing a threaded portion of one or more screws of the screw-rod configuration into one or more of a plurality of vertebrae of an organic body;
   securing a rod of the screw-rod configuration to a head portion of the one or more screws;
   securing an elongated portion of the first nail into a rib of the organic body, the rib adjacent to the screw-rod configuration; and
   securing a head portion of the first nail to the rod of the screw-rod configuration.

2. The method of claim 1, wherein the first nail extends substantially orthogonally from the rod.

3. The method of claim 1, wherein the head portion of the first nail is secured above the one or more screws.

4. The method of claim 1, further comprising:
   securing an elongated portion of a second nail to a second rib adjacent to the screw-rod configuration; and
   securing a head portion of the second nail to the rod of the screw-rod configuration.

5. The method of claim 4, wherein the first nail and second nail are dimensioned differently.

6. The method of claim 4, wherein the first nail and second nail have the same dimensions.

7. The method of claim 1, wherein the head portion of the first nail is secured between a first and second of the one or more screws.

8. The method of claim 1, wherein the head portion of the first nail is secured below the one or more screws.

* * * * *